(12) United States Patent
de Laat et al.

(10) Patent No.: US 11,104,969 B2
(45) Date of Patent: Aug. 31, 2021

(54) FORMULATION AID

(71) Applicant: Coöperatie Koninklijke Cosun U.A., Breda (NL)

(72) Inventors: Adrianus Marinus Maria de Laat, Oisterwijk (NL); Bartholomeus Mattheus de Roode, Rotterdam (NL); Tom Willem Louis Brooijmans, Breda (NL)

(73) Assignee: COÖPERATIE KONINKLI JKE COSUN U.A., Breda (NL)

( * ) Notice: Subject to any disclaimer, the term of this patent is extended or adjusted under 35 U.S.C. 154(b) by 290 days.

(21) Appl. No.: 16/350,210

(22) Filed: Oct. 16, 2018

(65) Prior Publication Data
US 2019/0161814 A1 May 30, 2019

(30) Foreign Application Priority Data
Oct. 16, 2017 (EP) .................................... 17196700

(51) Int. Cl.
| | | |
|---|---|---|
| C13B 15/00 | (2011.01) | |
| C13B 15/02 | (2011.01) | |
| A61K 36/21 | (2006.01) | |
| A61K 9/20 | (2006.01) | |
| A61K 36/28 | (2006.01) | |
| C11D 17/06 | (2006.01) | |
| C11D 17/00 | (2006.01) | |
| C11D 3/382 | (2006.01) | |
| C13B 10/08 | (2011.01) | |

(52) U.S. Cl.
CPC ............ *C13B 15/02* (2013.01); *A61K 9/2068* (2013.01); *A61K 36/21* (2013.01); *A61K 36/28* (2013.01); *C11D 3/382* (2013.01); *C11D 17/0073* (2013.01); *C11D 17/0091* (2013.01); *C11D 17/06* (2013.01); *C13B 10/08* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 4,770,886 A | * | 9/1988 | Lee .......................... | A23L 33/22 134/10 |
| 2005/0074542 A1 | * | 4/2005 | Lundberg ................. | D21C 3/02 426/658 |
| 2013/0115397 A1 | * | 5/2013 | Holmes ..................... | C08L 5/06 428/35.6 |

* cited by examiner

*Primary Examiner* — Stefanie J Cohen (74) *Attorney, Agent, or Firm* — Foley & Lardner LLP (57) ABSTRACT

This invention relates to new formulation aids, as well as to the production thereof, to the uses thereof and to the formulations comprising them.

20 Claims, 4 Drawing Sheets

FORMULATION AID

FIELD OF THE INVENTION

This invention relates to new formulation aids, as well as to the production thereof, to the uses thereof and to the formulations comprising them.

BACKGROUND OF THE INVENTION

In chemistry, and related fields, the term 'formulation' is broadly understood as the mixing or combining of two or more components into appropriate structures. Such structures (or formulations) may be created for diverse purposes, such as to impart specific properties when the formulation is put into use; to improve handling properties during processing; to improve stability; etc. Formulation development is often essential for putting a substance or composition with a certain (potential) utility to actual (e.g. commercial) use. Formulation development has become an art per se in technical fields such as pharmaceutical products, cosmetics, coatings, dyes, alloys, cleaning agents, foods, lubricants, fuels, fertilizers, pesticides and many others.

Well known examples of formulations in these fields include tablets, powders, granulates, composites, liquids, pastes, gels, etc. In such formulations (usually) a clear distinction can be made between the substance(s) of primary interest, usually referred to as the active component(s) or active ingredient(s), and components that are primarily needed to present the active component(s) in a suitable structure/formulation. Such components characteristically would not have any utility without the active component(s), even though their presence might be essential for proper functioning thereof upon use of the formulation. There are quite a number of general terms commonly used to refer to these 'inactive' components, such as 'formulation aid', 'excipient', 'adjuvant', etc. Examples include bulking aids, tableting aids, anti-caking aids, dispersing aids, etc. Formulation aids may contribute to the properties of a formulation in more than one way.

Formulations are often developed to meet diverse requirements that are not seldom contradictory. This is for instance the case in tableting technology. In the production of tablets, aids are required to confer not only good flow properties and binding capacity but also a high uptake capacity for active substances which are difficult to compress. Often tablets, at the same time, are intended to have a short disintegration time, low friability, high fracture resistance and rapid release of active substance upon use. High fracture resistance is, for example, associated with the presence of many points of contact of bulking aid and binder inside the tablet, which can be achieved only if the bulking aid and binder is in the form of fine particles. Fine-particle substances in turn have poor flow properties. Frequently a combination of different formulation aids is needed to find the best compromise between such 'conflicting' properties. There has been no lack of attempts to develop multipurpose tableting aids that can be used to confer various properties simultaneously. Multipurpose tableting aids typically consist of a plurality of components that are 'pre-blended' in specific manufacturing processes.

There remains a significant interest in the development of new aids that can be used in the production of tablets and other formulations to confer advantageous properties to such formulations in a simple and versatile manner. Preferably such new aids can be obtained using simple, low-cost and environmentally acceptable processes.

It is an object of the present invention to provide such improved formulation aids.

SUMMARY OF THE INVENTION

The present inventors have surprisingly found that a formulation aid with highly advantageous properties can be produced from certain plant derived materials using a convenient and economically attractive process.

More in particular, it has been found that certain parenchymal cell wall containing plant materials can be processed into a formulation aid by specific and relatively simple drying and milling operations.

The raw materials used in accordance with the invention typically are obtained as a byproduct in conventional processing of certain agricultural products into food ingredients and/or food products. These materials nowadays are mostly used as e.g. animal feed. In accordance with the present invention, the economic value of these byproducts is thus significantly enhanced. At the same time, the formulation aid of the present invention will constitute a technically viable alternative for existing formulation aids produced using materials and processes that overall impose a (significantly) higher environmental burden.

Irrespective of these economic and environmental considerations, the formulation aid of the present invention provides significant technical/functional advantages over existing formulation aids, which become evident, for instance, when applied as tableting aid and/or anti-caking aid. As shown, in the appending examples, the present formulation aid, when used as a tableting aid, exhibits an improved combination of properties such as extremely low friability combined with good hardness and disintegration capabilities. Furthermore, the present formulation aid, amongst other things, is highly effective as an anti-caking agent.

In the prior art efforts have been described to convert sugar beet pulp and similar plant derived materials into products valuable for other industries. U.S. Pat. No. 5,213,836, for example, describes a method of preparation of sugar beet formulation aid for use as a non-caloric, non-coloring, bland ingredient in foodstuffs. U.S. Pat. No. 4,451,489 describes a process for producing a non-caloric sugar beet pulp bulking agent.

The processes of the present invention have, to the inventors' best knowledge, never been described in the art nor have the materials resulting there from.

The present invention thus relates to the formulation aid as obtained by a process comprising drying parenchymal cell wall containing plant material pulp at moderate temperatures (not exceeding 95° C.) followed by milling or comminuting the dried pulp, to the process itself, to the uses of the present formulation aid and to products (formulations) comprising the present formulation aid.

These and other aspects of the invention will become apparent on the basis of the following detailed description and the appended examples.

DETAILED DESCRIPTION OF THE INVENTION

A first aspect of this invention thus concerns a formulation aid in the form of a powder, which is derivable from parenchymal cell wall containing plant materials.

A further aspect of this invention concerns a method of producing a formulation aid in the form of a powder from a parenchymal cell wall containing plant material, the method comprising:

a) providing a quantity of hydrated pulp derived from a parenchymal cell wall containing plant material;
b) subjecting said hydrated pulp to a drying step, during which the temperature of the composition does not exceed 95° C.; and
c) subjecting the pulp as obtained in step b) to a milling or comminuting process to produce a powder.

A further aspect of this invention concerns the formulation aid that is obtainable by the methods as defined herein.

As used herein, the term 'formulation aid' is used to denote the specific product of the present invention, which may advantageously be applied as an additive, adjuvant or excipient in the production/creation of formulations of other, typically 'active' components. It will be understood that the term is used for ease of reference and does not limit the scope of the invention per se. In particular it does not mean that identical products intended for other purposes would not be covered by the invention. Whenever, in this document, reference is made to the 'formulation aid' this refers to the product as described herein on the basis of structural/chemical characteristics as well as to the products obtainable by the process described herein, which may be the same or different products, as will be understood by those skilled in the art. In particular, a property may be inherent to the materials obtained using the process described herein, without said property being described herein in an explicit way.

The formulation aid of the invention is a processed parenchymal cell wall plant material. The formulation aid of the present invention typically has the form of a powder, preferably a free-flowing powder. Typically, the formulation aid of the invention has the form of a powder comprising discrete particles with a characteristic composition, structure, morphology, particle size distribution, etc. As will be understood by those skilled in the art, these characteristics are influenced by the choice of the plant material and by the methods applied to process them. Furthermore, these characteristics and, consequently, the processing will determine the functional properties.

The formulation aid of this invention is derived from parenchymal cell containing plant material. Parenchymal cell walls contain relatively thin cell walls (compared to secondary cell walls) which are tied together by pectin. Secondary cell walls are much thicker than parenchymal cells and are linked together with lignin. This terminology is well understood in the art. Polysaccharides typically make up 90% or more of the primary plant cell walls, cellulose, hemicelluloses and pectins being the main constituents. The precise morphology and (chemical) make-up of parenchymal cell walls may vary from species to species. The parenchymal cell wall plant material of this invention may be obtained from a variety of plant sources containing parenchymal cell walls. Parenchymal cell wall, which may also be denoted as 'primary cell wall', refers to the soft or succulent tissue, which is the most abundant cell wall type in edible plants. The basic process of the invention may be generally described as providing a novel and improved formulation aid from hydrated pulp from sugar beet, citrus fruits, tomatoes, chicory, potatoes, pineapple, apple, cranberries, grapes, carrots and the like (exclusive of the stems, and leaves). For instance, in sugar beets, the parenchymal cells are the most abundant tissue surrounding the secondary vascular tissues. The parenchymal cell wall plant material in accordance with the invention is preferably a material obtained from sugar beet, citrus fruit, tomato, chicory, potato, pineapple, apple, cranberry, citrus, grape and/or carrot, more preferably a material obtained from sugar beet and/or chicory, most preferably it is a material obtained from sugar beet, e.g. as a by-product of sucrose production.

Since the processing in accordance with the present invention is presumed not to substantially affect the dry matter composition of the parenchymal cell wall containing plant material, it is believed that the formulation aid will have a composition largely corresponding to that of the untreated material or the pulp, having cellulose, pectin and hemicellulose as the main fiber constituents.

The term "cellulose" as used herein refers to homogeneous long chain polysaccharides comprised of β-D-glucose monomer units, of formula $(C_6H_{10}O_5)_n$, and derivatives thereof, usually found in plant cell walls in combination with lignin and any hemicellulose. The linear array of β-D-glucose units into chains is referred to as the primary structure and is shared by all cellulose materials. The arrangements of chains of glucose units into a crystalline or amorphous zone constitutes the secondary structure. The regional variation in secondary structure throughout a material (e.g. regions of varying crystallinity dispersed among areas of amorphous cellulose) together with the network formed by hemicellulose and pectin defines its tertiary structure. Accordingly, structures such as fibrils, bundles, sheets, and the like may be seen to comprise tertiary structures. The cell wall of a parenchymal cell is best described as a tertiary structure. The formulation aid of this invention may be obtained from a variety of plant sources containing parenchymal cell walls. Parenchymal cell wall, which may also be denoted as 'primary cell wall', refers to the soft or succulent tissue, which is the most abundant cell wall type in edible plants. Preferably the formulation aid comprises, by dry weight, at least 15 wt %, preferably 15-40 wt %, more preferably 15-35 wt %, most preferably 15-30 wt % of cellulose.

The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the L-rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-I fraction. Preferably the formulation aid of the present invention comprises, by dry weight, at least 15 wt %, preferably 15-40 wt %, more preferably 15-35 wt %, most preferably 15-30 wt % of pectin.

The term "hemicellulose" refers to a class of plant cell-wall polysaccharides that can be any of several homo- or heteropolymers. Typical examples thereof include xylane, arabinane xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in molecular weight than cellulose and cannot be extracted by hot water or chelating agents, but can be extracted by aqueous alkali. Preferably the formulation aid of the present invention comprises, by dry weight, at least 15 wt %, preferably 15-40 wt %, more preferably 15-35 wt %, most preferably 15-30 wt % of hemicellulose.

In a preferred embodiment of the invention, the relative amounts of the cellulose, pectin and hemicellulose in the formulation aid is similar to that of common sugar beet pulp, comprising 15-35 wt %, preferably 20-30 wt %, more preferably 22-26 wt % celullose, 15-35 wt %, preferably 20-30 wt %, more preferably 22-26 wt % hemicelullose and 15-35 wt %, preferably 20-30 wt %, more preferably 21-25 wt % pectin.

Without wishing to be bound by any particular theory, it is believed that the particles essentially consist of fragments comprising clusters of collapsed/ruptured parenchymal cells, presumably with the cell wall structures largely or completely intact, i.e. at the primary, secondary and tertiary level. Hence, in embodiments of the invention, the fiber components of the particles are structured in largely, substantially or entirely the same way as they are in intact parenchymal cell walls. In embodiments of the invention, the formulation aid is characterized by the presence of structures wherein the tertiary structure of cellulose is not substantially affected.

Other typical, non- or sparingly soluble, parenchymal cell (wall) constituents that may be retained in the material in the processes of the invention, include protein, lignin, residual sugars and ash.

Hence, in an embodiment of the invention, a formulation aid as defined herein is provided comprising protein, typically in an amount within the range of 1-25 wt. %, based on total weight of the formulation aid, preferably 3-15 wt. %, more preferably 6-10 wt. % Hence, in an embodiment of the invention, a formulation aid as defined herein is provided comprising lignin, typically in an amount within the range of 0-10 wt. %, based on total weight of the formulation aid, preferably 0-6 wt. %, more preferably 0-3 wt. %.

Hence, in an embodiment of the invention, a formulation aid as defined herein is provided comprising residual sugars, typically in an amount of less than 10 wt. %, based on total weight of the formulation aid, preferably less than 6 wt. %, more preferably less than 3 wt. %. In an embodiment of the invention, a formulation aid as defined herein is provided comprising residual sugars, typically in an amount of more than 0.1 wt. %, based on total weight of the formulation aid, preferably more than 0.5 wt. %, more preferably more than 1 wt. %. The processing of the parenchymal cell wall containing plant material in accordance with the invention, typically results in removal of most or all of the water and water-soluble cell components. Typically, in accordance with the invention, the parenchymal cell wall containing plant material is processed in such a way as to provide a formulation aid which contains particles possessing a specific dry matter content. In a specific embodiment of the invention, the formulation aid has a dry matter content of more than 80 wt. %, based on the total weight of the material, preferably more than 85 wt. %, more preferably more than 90 wt. %, still more preferably more than 93 wt. %, more than 94 wt. % or more than 95 wt. %. There is no particular upper limit, i.e. with a view to the functional properties of the material. In practice, the drying step will be carried out in such a way to achieve a dry matter content of 100 wt. % or less, based on the total weight of the material, e.g. less than 99.5 wt. %, less than 99 wt. %, less than 98.5 wt. %, less than 98 wt. %, less than 97.5 wt. %, or less than 97 wt. %. A preferred method to measure dry matter content is the ICUMSA GS2/1/3/9-15 (2007) method which is known to the person skilled in the art.

Typically the formulation aid may contain some residual water without interfering with the free-flowing behavior of the (solid) powder product and/or the functional properties thereof. Typically, in embodiments of the invention, the water content is within the range of 1-12 wt. %, such as 2-10 wt. % or 4-6 wt. %.

Typically, in accordance with the invention, the parenchymal cell wall containing plant material is processed in such a way as to provide a formulation aid which contains particles possessing specific particle size characteristics.

In a specific embodiment of the invention, the formulation aid is such that no more than 10 vol % of particles have a particle size <30 μm, preferably <50 μm, most preferably <80 μm, as measured by laser diffractometry.

In another embodiment of the invention, the formulation aid is such that no more than 10 vol % of particles have a particle size >800 μm, preferably >700 μm, most preferably >600 μm, as measured by laser diffractometry. In accordance with the invention, the particle size distribution is typically determined by measuring with a laser light scattering particle size analyzer utilizing the Mie theory of light scattering, such as the Malvern Mastersizer or another instrument of equal or better sensitivity and reporting the data using a volume equivalent sphere model.

Typically, in accordance with the invention, the parenchymal cell wall containing plant material is processed in such a way as to provide a formulation with a specific density.

Typically, in accordance with the invention, the parenchymal cell wall containing plant material is processed in such a way as to provide a formulation aid which contains particles possessing a specific bulk density. In a specific embodiment of the invention, the formulation aid has a bulk density of >400 g/l, preferably >500 g/l, most preferably >600 g/l. Bulk density measurements are known to the person skilled in the art.

Typically, in accordance with the invention, the parenchymal cell wall containing plant material is processed in such a way as to provide a formulation aid which contains particles possessing a specific water holding capacity.

Water holding capacity (water absorption, water uptake, or water hydration or binding) is determined as the maximum amount of water that 1 g of material will imbibe and retain under low-speed centrifugation. Water holding capacity may be an important factor to assess properties such as anti-caking effect and swellability. In a specific embodiment of the invention, the formulation aid has a water holding capacity of >5 ml/g, preferably >6 ml/g, most preferably >7 ml/g. A preferred method to measure water holding capacity is the AACC International Approved Methods of Analysis, 11th Ed. Method 56-30.01 which is known to the person skilled in the art.

Typically, in accordance with the invention, the parenchymal cell wall containing plant material is processed in such a way as to provide a formulation aid which contains particles possessing a specific total fiber content.

In a specific embodiment of the invention, the formulation aid has a total fiber content of 70-80% by weight and a protein content of 5-10% by weight. A preferred method to measure total fiber content is the AOAC 991.43 method which is known to the person skilled in the art. A preferred method to measure protein content is the Kjeldahl method utilizing an N factor of 6.25, which is known to the person skilled in the art.

In an embodiment of the invention, the formulation aid is provided as a free flowing powder. The term "free-flowing powder", as used herein, is well known to those skilled in the art and includes particulate materials that can be poured (e.g., from one vessel having an opening of from about 10 cm² to 50 cm² to another vessel of similar dimensions) without substantial clumping of the particles.

In another aspect, this invention provides a method of producing a formulation aid in the form of a powder from a parenchymal cell wall containing plant material, the method comprising:

a) providing a quantity of hydrated pulp derived from a parenchymal cell wall containing plant material;
b) subjecting said hydrated pulp to a drying step, during which the temperature of the composition does not exceed 95° C.; and
c) subjecting the pulp as obtained in step b) to a milling or comminuting process to produce a powder.

In a preferred embodiment, the method described above is provided, wherein step a) comprises the production of hydrated pulp by a process comprising a1) slicing parenchymal cell wall containing plant material into cosettes, particles or strips and a2) subjecting said cosettes, particles or strips to an extraction step wherein the cosettes, particles or strips are contacted with an aqueous extraction liquid; and a3) separating a fraction of the liquid from the hydrated pulp.

As explained herein before, in certain embodiments of the invention, it is preferred that the parenchymal cell wall material is obtained from sugar beet pulp or chicory pulp. In a preferred embodiment, the method described above is provided, wherein step a) comprises the production of spent sugar beet pulp, preferably by a process comprising a1) slicing sugar beets into cosettes, particles or strips and a2) subjecting said cosettes, particles or strips to an extraction step wherein the cosettes, particles or strips are contacted with an aqueous extraction liquid; and a3) separating a fraction of the liquid from the hydrated sugar beet pulp.

In accordance with the invention, it is particularly preferred that the hydrated pulp is fresh pulp, e.g. fresh sugar beet pulp as obtained directly after extraction of the sugar in conventional sugar beet processing. Hence, in an embodiment of the invention, the hydrated pulp has not been dried and rehydrated after the extraction process. Furthermore, in an embodiment of the invention, the hydrated pulp has not been subjected to aerobic and/or anaerobic fermentative processes. For example, the pulp has not been subjected to ensiling processes or the like. In a preferred embodiment of the invention, the hydrated pulp is unmolassed, i.e. no molasses have been added to the pulp after sugar extraction. Furthermore, in accordance with the invention, the pulp preferably has not been subjected to any chemical treatment following conventional processing, e.g. following extraction of the sugar in the case of sugar beet pulp. More in particular, it is preferred that the pulp and the plant material from which it is derived are not subjected to any chemical treatment resulting in the removal and/or degradation of significant amounts of pectin and/or hemicellulose prior or during any step in the present process.

In accordance with the invention, the hydrated pulp typically has a dry matter content within the range of 15-40 wt. %, based on the total weight of the material, more preferably within the range of 20-32 wt. %, most preferably within the range of 21-26 wt. %.

In accordance with the invention, the slices in the hydrated pulp typically possess a major dimension of 0.1-200 mm, preferably 1-50 mm, more preferably 5-20 mm. In preferred embodiments, 80 wt. %, more preferably 90%, most preferably 95% of the slices possesses a major dimension according the aforementioned ranges.

In an embodiment of the invention a method as defined herein is provided wherein step b) comprises drying the hydrated pulp to a dry matter content of more than 80 wt. %, based on the total weight of the material, preferably more than 85 wt. %, more preferably more than 90 wt. %, still more preferably more than 93 wt. %, more than 94 wt. % or more than 95 wt. %. There is no particular upper limit, i.e. with a view to the functional properties of the material. In practice, the drying step will be carried out in such a way to achieve a dry matter content of 100 wt. % or less, based on the total weight of the material, e.g. less than 99.5 wt. %, less than 99 wt. %, less than 98.5 wt. %, less than 98 wt. %, less than 97.5 wt. %, or less than 97 wt. %.

As indicated before, the temperature at which the hydrated pulp is dried is believed to affect the chemical, structural and/or functional properties of the formulation aid obtained. In accordance with the invention the temperature of the material during the drying step is typically kept below 95° C. In an embodiment of the invention a method as defined herein is provided wherein step b) comprises a thermal drying treatment wherein the composition comprising the hydrated pulp is heated to a temperature within the range of 30-95° C., more preferably within the range of 40-92.5° C., more preferably within the range of 50-90° C., more preferably within the range of 60-87.5° C., most preferably within the range of 70-85° C. In certain embodiments of the invention a method as defined herein is provided wherein step b) comprises a thermal drying treatment wherein the composition comprising the hydrated pulp is subjected to temperatures as defined here above. In certain embodiments of the invention a method as defined herein is provided wherein step b) comprises a thermal drying treatment wherein the composition comprising the hydrated pulp is placed in a dryer which is operated at temperatures as defined here above.

Typically, in accordance with the invention, the drying step is performed using industrial drying equipment known to the skilled person such as a rotary dryer, static oven, fluidized bed, rolling bed, conduction dryer, convection dryer, conveyer oven, belt dryer etc.

Preferably a dryer is used that achieves heat transfer and/or moisture removal by a gentle thermal treatment, such as by convection utilizing warm or hot air. Hence, in one embodiment of the invention step b) comprises subjecting said hydrated pulp to a drying step wherein the hydrated pulp is placed in an environment with an air temperature within the range of 30-95° C., more preferably within the range of 40-92.5° C., more preferably within the range of 50-90° C., more preferably within the range of 60-87.5° C., most preferably within the range of 70-85° C. In one embodiment of the invention step b) comprises subjecting said hydrated pulp to a drying step wherein the hydrated pulp is contacted with air heated to the aforementioned temperatures. In one embodiment of the invention step b) comprises subjecting said hydrated pulp to a drying step using a convection oven. In a preferred embodiment of the invention, step b) is performed using equipment wherein the pulp is not subjected to significant or substantial mechanical impact. Preferably the dryer is a continuous drying apparatus. In a particularly preferred embodiment of the invention, the dryer is a belt dryer wherein warm/hot air is used to dry the material while it is being transported over a belt.

In certain embodiments of the invention a method as defined herein is provided wherein step b) comprises a thermal drying treatment wherein the composition comprising the hydrated pulp is placed in a dryer which is operated at atmospheric pressure.

As will be understood by those skilled in the art based on the present teachings, the time needed to achieve the target water level in step b) will depend, amongst others, on the water content of the hydrated pulp before drying, on the exact nature of the pulp, on the temperature and pressure applied, etc. It is within the capabilities of those of average skill in the art to carry out the process taking account of these variables. In an embodiment of the invention, a method as defined herein is provided wherein step b) comprises a thermal drying treatment wherein the hydrated pulp is subjected to heating under conditions and for a period of time sufficient to reach a dry matter content of more than 80 wt. %, based on the total weight of the material, preferably more than 85 wt. %, more preferably more than 90 wt. %, still more preferably more than 93 wt. %, more than 94 wt. % or more than 95 wt. %.

As will be understood by those skilled in the art based on the present teachings, in order to improve the economic feasibility of the present methods, it may be preferable to subject the hydrated pulp to a mechanical dewatering treatment, which will reduce the amount of heat/energy needed in the thermal drying step. Hence, in an embodiment of the invention, a method as defined herein is provided wherein step b) comprises a mechanical dewatering treatment preceding the thermal drying treatment. Conventional mechanical dewatering treatments may be applied in accordance with the invention, such as centrifuging, filter-pressing. In an embodiment of the invention, a method as defined herein is provided wherein step b) comprises a mechanical dewatering treatment, preceding the thermal drying treatment.

In accordance with the invention, the dried material as obtained in step b) is subjected to a mechanical treatment step, resulting in a product in the form of a powder, typically a free-flowing powder, having the target particle size and/or density characteristics. Preferably, the treatment primarily affects the macroscopic size of the particles and does not substantially affect the material's primary, secondary and/or tertiary structures characteristic of parenchymal cell wall material. Changes in the primary, secondary and/or tertiary structures may be brought about by high shear force treatments. In general, conventional milling or comminuting treatments performed to achieve the particle size and/or density characteristics as defined herein elsewhere will typically not result in such changes in the primary, secondary and/or tertiary structures characteristic of parenchymal cell wall material.

Typically, in accordance with the invention, the milling or comminuting process is performed using industrial particle size reduction techniques known to the skilled person such as grinding, milling, crushing or the like, known in the art. Preferred methods include grinding using stirring blades such as unidirectional rotary-, multiaxis rotary-, reciprocal inverse-, vertical motion-, rotary and vertical motion-, and duct line-system stirring blades, such as portable mixers, solid mixers and vertical motion-, and duct line-system stirring blades; screen system crushing; impact crushing; cage milling; hammer milling; rotary extrusion system grinding using kneaders; screen milling; etc. These methods may be used alone or in combination. Preferably the milling or comminuting method is hammer milling.

There are also technological solutions for drying and grinding in one machine such as flash drying. Hence, embodiments are also envisaged wherein steps b) and c) can be performed simultaneously, so as to produce a powder composition having the target specifications as defined above.

Typically, in accordance with the invention, the milling or comminuting process is controlled to yield particles of a specific size. In a specific embodiment of the invention, the milling or comminuting process is carried out such that no more than 10 vol % of particles have a particle size <30 µm, preferably <50 µm, most preferably <80 µm, as measured by laser diffractometry. In another embodiment of the invention, the milling or comminuting process is carried out such that no more than 10 vol % of particles have a particle size >800 µm, preferably >700 µm, most preferably >600 µm, as measured by laser diffractometry.

The particle size distribution may be influenced by performing an additional step to select particles by size, e.g. to remove large particles or dust/fines. Conventional sieving techniques may be applied in accordance with the invention, such as centrifugal sifting, gyratory sifting, vibrating sifting, ultrasonic sifting etc. In an embodiment of the invention, a method as defined herein is provided wherein step c) is followed by sieving.

Typically, in accordance with the invention, the milling or comminuting process is controlled to yield particles possessing a specific bulk density. In a specific embodiment of the invention, the milling or comminuting process is carried out such that the powder has a bulk density of >400 g/l, preferably >500 g/l, most preferably >600 g/l.

After completion of step c) a material is obtained that has advantageous properties for use as a formulation aid, e.g. as a tableting aid and/or an anti-caking aid. To exploit these properties, the formulation aid may simply be packaged and distributed to (e.g.) processors producing products in the form of tablets, powders, etc. Alternatively, the formulation aid may be combined with one or more other adjuvants/excipients that further enhance the functional properties of the composition as a formulation aid.

Thus, in another aspect, the invention provides products comprising the formulation aid of the present invention and at least one further substance or component.

In one embodiment, the invention provides a tablet comprising the formulation aid of the present invention, preferably a compressed tablet comprising the formulation aid. The formulation aid of the present invention enables the individual ingredients of a tablet to form a homogenous entity, effectively acting as a binder. Tablets comprising the formulation aid of the invention, at the same time advantageously have a low friability and sufficient hardness. The inventors have found that the formulation aid according to the invention possesses advantageous water absorption and swellability properties. When incorporated as a component in a tablet, the rapid water absorption observed with the formulation aid of the present invention will cause the formulation aid to swell and create internal stress points that will break up the tablet. This may be of use, for example, in the formulation of tablets which require disintegration in aqueous environment, such as dishwasher or laundry tablets. Thus, in another aspect of the invention, the use of the formulation aid as a disintegrant is provided.

In accordance with the invention, the tablet may be a medicinal/pharmaceutical or neutraceutical product, for human and/or veterinary use; a detergent product, e.g. a dishwashing tablet, a laundry tablet, a descaling tablet, a chlorine tablet, a mineral tablet, a bleach tablet, a moisture absorber tablet, a fertilizer tablet etc.

In accordance with the invention, the tablet may be a single-layer, multi-layer such as double layer and triple layer, core (tab-in-tab) tablet.

Without wishing to be bound by any theory, it is believed that the lower friability observed for tablets utilizing the formulation aid according to the invention (as shown in the examples) is of additional benefit when using unconventionally shaped or sculpted tablets. Hence, in an embodiment of the invention, the tablet may be a free shape such as bone shape, animal shape, star shape, face shape, sculpted etc. tablet.

As explained herein elsewhere, it has been found that tablets formulated with the formulation aid of the present invention combine highly desirable properties such as low friability (thus preventing damage to the tablets during transport or handling) and high disintegration. The formulation aid of the present invention confers these and/or other beneficial properties already when used in relatively small relative amounts. On the other hand, embodiments are envisaged, wherein the formulation aid of the present invention also constitutes a major ingredient, e.g. when it is used as a filler or bulking agent in pharmaceutical tablets containing very small quantities of active ingredient. Hence, the relative amount of the formulation aid in a tablets according to the present invention may vary over a wide range. In a preferred embodiment of the invention, the formulation aid is present in the tablet in an amount within the range of 0.05-99 wt. %, based on the total weight of the tablet, preferably 0.1-50 wt. %, 0.2-25 wt. %, 0.3-20 wt. %, 0.4-15 wt. % or 0.5-10 wt. %.

In an embodiment of the invention, a tablet is provided as defined herein before, wherein the tablet is a pharmaceutical/medicinal tablet, comprising the formulation aid of the present invention, in conjunction with one or more active pharmaceutical ingredients ('APIs'), such as the compounds included in the Anatomical Therapeutic Chemical (ATC) classification system, maintained by the World Health Organization.

In an embodiment of the invention, a tablet is provided as defined herein before, wherein the tablet is a nutraceutical or food supplement tablet, comprising the formulation aid of the present invention, in conjunction with one or more physiologically active ingredients, such as vitamins, minerals, trace elements, and/or one or more food-grade excipients, such as a compound which is recognized by the U.S. Food & Drug administration as GRAS (Generally Recognized as safe).

In an embodiment of the invention, a tablet is provided as defined herein before, wherein the tablet is a dishwashing tablet, comprising the formulation aid of the present invention, in conjunction with one or more ingredients selected from the group consisting of phosphates, bleaching agents, ionic surfactants, non-ionic surfactants, enzymes, alkaline salts, anti-foaming agents, complexing agents, perfumes, anti-caking agents, starches, gelling agents, emulsifiers, dispersing agents, sand etc.

In an embodiment of the invention, a tablet is provided as defined herein before, wherein the tablet is a laundry tablet, comprising the formulation aid of the present invention, in conjunction with one or more ingredients selected from the group consisting of phosphates, bleaching agents, optical brighteners, ionic surfactants, non-ionic surfactants, enzymes, alkaline salts, anti-foaming agents, complexing agents, perfumes, anti-caking agents, starches, gelling agents, emulsifiers, dispersing agents, dye transfer inhibitors, fabric softeners, colorants, etc.

In an embodiment of the invention, a tablet is provided as defined herein before, wherein the tablet is a fertilizer tablet, comprising the formulation aid of the present invention, in conjunction with one or more ingredients selected from the group consisting of ammonium compounds, urea compounds, magnesium compounds, potassium compounds, copper compounds, and zinc compounds.

In an embodiment of the invention, a tablet is provided as defined herein before, wherein the tablet is a descaling tablet, comprising the formulation aid of the present invention, in conjunction with one or more ingredients selected from the group consisting of descaling agents, complexing agents, chelating agents, binders, fillers, acidic compounds such as hydrochloric acid, acetic acid, citric acid, glycolic acid, formic acid, phosphoric acid and sulfamic acid. The present inventors found that in these kinds of applications, the formulation aid of the present invention not only improves the properties of the tablet but also has the capability of chelating/binding bivalent and trivalent free metal ions.

In an embodiment of the invention, a tablet is provided as defined herein before, wherein the tablet is a chlorine tablet, comprising the formulation aid of the present invention, in conjunction with one or more ingredients selected from the group of chlorine compounds, such as chlorinated isocyanurates, hypochlorite salts, chlorine dioxide, chloride of lime; etc.

In an embodiment of the invention, a tablet is provided as defined herein before, wherein the tablet is a mineral tablet, comprising the formulation aid of the present invention, in conjunction with one or more ingredients selected from the group consisting of minerals of calcium, phosphorus, potassium, sodium, iron, cobalt, copper, zinc, manganese, molybdenum, iodine, and selenium, bromine, arsenic, nickel, fluorine, boron, lithium, strontium.

In an embodiment of the invention, a tablet is provided as defined herein before, wherein the tablet is a bleach tablet, comprising the formulation aid of the present invention, in conjunction with one or more ingredients selected from the group consisting of chlorine-based bleaches, peroxide-based bleaches, reducing bleaches, peracetic acid, ozone and combinations thereof. Chlorine-based bleaches may comprise hypochlorite compounds such as calcium hypochlorite, chlorine dioxide, etc. Peroxide-based bleaches may comprise hydrogen peroxide, sodium percarbonate and sodium perborate. Reducing bleaches may comprise sodium dithionite and sodium oxymethylene sulfoxylate.

In an embodiment of the invention, a tablet is provided as defined herein before, wherein the tablet is a moisture absorber tablet, comprising the formulation aid of the present invention, in conjunction with one or more ingredients selected from the group consisting of humectants, deliquescent compounds, hydratable compounds, carriers, activated carbon, oxygen absorbers, binders, antimicrobial agents, coatings. Suitable humectant salts may comprise calcium chloride, lithium chloride, sodium chloride, potassium sulfate, potassium carbonate and mixtures thereof.

In another embodiment of the invention, a formulation, comprising the formulation aid of the present invention and at least one further substance or component is provided wherein the formulation is a free flowing powder.

In another embodiment of the invention a tableting aid comprising the formulation aid of the present invention in conjunction with one, two, three, four or more component(s) selected from the group consisting of antiadherents, binders, coatings, colours, disintegrants, flavors, glidants, lubricants, preservatives, sorbents, sweeteners, fillers, flow regulating agents, bulking agents and other excipients is provided.

As explained herein elsewhere, it has been found that the use of the formulation aid in a powder or granulate formulation significantly reduces the tendency of such formulation to cake and/or form lumps during storage. In a preferred embodiment, powdered material containing the formulation aid of the present invention remains freely flowable even when stored under pressure and/or at varying ambient conditions. The formulation aid of the present invention can therefore also be used as to improve flowability of powders, avoiding or reducing blockage during conveying, storage and/or filling thereof and/or avoiding difficulties in dosing. These advantageous properties may for instance be exploited to influence the properties of powdered products such as food ingredient formulations; laundry detergent formulations; dish washing powders etc. In other aspects according to the invention, these advantageous properties may be exploited in the manufacture of medicinal/pharmaceutical or neutraceutical products, for human and/or veterinary use; a dishwashing tablet or a laundry tablet; a descaling tablet; a chlorine tablet; a mineral tablet, a bleach tablet; a humidity absorber tablet; a fertilizer tablet etc. The formulation aid of the present invention confers these and/or other beneficial properties already when used in relative small relative amounts. The relative amount of the formulation aid in a powder and/or granulate according to the present invention may vary over a wide range. In a preferred embodiment of the invention, the formulation aid is present in the tablet in an amount within the range of 0.05-25 wt. %, based on the total weight of the formulation, preferably 0.1-15 wt. %, 0.2-10 wt. %, 0.3-5 wt. %, 0.4-2.5 wt. % or 0.5-2 wt. %.

In an embodiment of the invention, a powder formulation or a granulate is provided as defined herein before, comprising the formulation aid of the present invention, in conjunction with a second component. In an embodiment of the invention, a powder formulation or a granulate is provided as defined herein before, comprising the formulation aid of the present invention, in conjunction with a second component, wherein said second component is moderately or highly hygroscopic or deliquescent. The term "hygroscopic" as used herein refers to materials that absorb significant amounts of atmospheric moisture when exposed to conditions of normal ambient relative humidity (RH), for example 10-50% RH. The moisture uptake is measured e.g. by dynamic vapor sorption at room temperature. In an embodiment of the invention, a hygroscopic component is a component displaying a weight increase (at equilibrium) of at least 0.5, 1, 2.5 or 5 wt. %, based on the total weight, in the 10-50% RH trajectory (at room temperature). The term "deliquescent" refers to components that tend to undergo gradual dissolution and/or liquefaction due to attraction and/or absorption of moisture from air when exposed to these conditions.

As will be understood by those skilled in the art, similar advantages may be achieved when using the present formulation aid in other types of coatings. Hence, in an embodiment of the invention formulations are provided comprising or consisting of coated particles, comprising a core surrounded by a coating comprising the formulation aid of the present invention. In a preferred embodiment of the invention, the formulation aid may be present in such formulation in an amount within the range of 0.05-25 wt. %, based on the total weight of the formulation, preferably 0.1-15 wt. %, 0.2-10 wt. %, 0.3-5 wt. %, 0.4-2.5 wt. % or 0.5-2 wt. %.

The inventors also envisage the incorporation of the formulation aid according to the invention in composites, to influence the properties of other materials such as plastics; resins; materials consisting of or comprising carbon fibre, carbon nanotubes aramid fibers, glass fibres, hemp fibres, flax fibres and/or wood sheet etc. These properties include but are not limited to tensile modulus, yield stress, yield strain, stress at break, strain at break, charpy impact strength at various temperatures, charpy notched impact strength at various temperatures, coefficient of linear thermal expansion (normal and parallel), thermal conductivity, burning behaviour and, for thermoplastics, melting and glass transition temperature. Hence, in an embodiment of the invention, a plastic composite is provided comprising the formulation aid of the present invention in conjunction with at least one type of plastic, such as a resinous plastic. In accordance with the invention, the formulation aid is typically present in an amount within the range of 0.05-25 wt. %, based on the total weight of the plastic composite, preferably 0.1-15 wt. %, 0.2-10 wt. %, 0.3-5 wt. %, 0.4-2.5 wt. % or 0.5-2 wt. %.

In another aspect, the invention provides uses of the formulation aid of the present invention in accordance with what has been discussed elsewhere. Hence, as will be understood by those skilled in the art, based on the present disclosure, specific embodiments of the invention relate to the use of a formulation aid as defined herein, including a formulation aid obtainable by the methods as defined herein, for one or more of the following:

- as a formulation aid;
- for improving the properties of a formulation;
- as a tableting aid;
- for improving one or more properties of a compressed tablet, in particular friability, hardness and/or disintegration properties;
- for lowering friability of a compressed tablet;
- as a friability lowering agent in a compressed tablet
- for increasing hardness of a compressed tablet;
- as a hardness enhancer in a compressed tablet
- for improving disintegrating properties of a compressed tablet;
- as a disintegrating agent or disintegrant in a compressed tablet
- as a binder or binding agent in a compressed tablet
- as an excipient of adjuvant for a free flowing powder formulation or granulate
- for improving flowability and/or flowing behavior of a powder formulation or granulate
- as an anti-caking agent for a for a free flowing powder formulation or granulate
- for preventing caking or lump formation in a powder formulation or granulate
- as a coating ingredient
- as a water activity lowering agent in a solid formulation
- for improving the storage stability of a solid formulation and/or for extending the shelf life of a formulation;
- for complexing or chelating bi- or trivalent metal ions
- as a complexing or chelating agent
- for improving the properties of a plastic material, in particular in respect of one or more of the following properties: tensile modulus, yield stress, yield strain, stress at break, strain at break, charpy impact strength at various temperatures, charpy notched impact strength at various temperatures, coefficient of linear thermal expansion (normal and parallel), thermal conductivity, burning behaviour and, for thermoplastics, melting and glass transition temperature
- as a plastic composite component.

In another aspect of the invention, methods are provided for producing a formulation, such as the formulations described here above, said process comprising adding the formulation aid of the present invention with one or more further ingredients. Such methods will further typically comprise steps to homogeneously blend the formulation aid and the one or more further ingredients. In some embodiments of the invention, such methods will further typically comprise steps to form shaped articles or bodies from the combination of the formulation aid and the one or more further ingredients, e.g. by direct compression or by a coating or pelletizing process or the like.

In another aspect of the invention, methods are provided for improving one or more properties of a formulation, such as the formulations described here above, said process comprising incorporating into the formulation, the formulation aid of the present invention.

Thus, the invention has been described by reference to certain embodiments discussed above. It will be recognized that these embodiments are susceptible to various modifications and alternative forms well known to those of skill in the art. Many modifications in addition to those described above may be made to the structures and techniques described herein without departing from the spirit and scope of the invention. Accordingly, although specific embodiments have been described, these are examples only and are not limiting upon the scope of the invention. Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The following examples are offered for illustrative purposes only, and are not intended to limit the scope of the present invention in any way.

EXAMPLES

Example 1—Production of Formulation Aid According to the Invention

Production

Formulation aid according to the invention was produced from fresh sugar beet pulp obtained as a side product from a regular sugar extraction process. The hydrated beet pulp is unmolassed, had not been silaged and is received with a dry matter content of approximately 22%.

1000 kg hydrated beet pulp was dried by means of a belt dryer wherein warm/hot air is used to dry the material while it is being transported over a belt to a dry matter content of approximately 94%, resulting in approximately 225 kg dried beet pulp. The dried beet pulp was subjected to hammer milling and subsequently sieved through a 600 μm sieve to result in approximately 202 kg formulation aid according to the invention.

Characterization

The dry matter content was established at 94%±2% using the ICUMSA GS2/1/3/9-15 (2007) method.

The particle distribution was determined using a Malvern Mastersizer laser light scattering particle size analyzer and is characterized by 10 vol % of particles having a particle size <85 μm and 10 vol % of particles having a particle size >564 μm.

The bulk density was determined as 650-700 g/l

The water holding capacity was established at 7-8 ml/g using the AACC International Approved Methods of Analysis, 11th Ed. Method 56-30.01.

Example 2—Dishwasher Tablets

Compacted dishwasher tablets containing the formulation aid according to the present invention were evaluated for hardness, friability and disintegration rate and compared with diverse commercially available tableting aids and a control (Sokalan PA 25 homopolymer (90% active)) in order to establish the multifunctionality of the formulation aid of the present invention.

Composition of Tablets

The composition of the tablets is shown in the below table.

| Component | wt % |
| --- | --- |
| Sodium citrate | 16 |
| Sodium carbonate | 30 |
| Sodium percarbonate | 10 |
| Methylglycinediacetic acid (MGDA, 78% active) | 25 |
| tableting aid | 10 |
| Tetraacetylethylenediamine | 2.5 |
| Surfactants | 4 |
| Enzymes | 2.5 |
| Sodium sulfate | q.s. |

The tableting aid in the above composition was formulated according to the below table (fractions by weight).

| Batch | Formulation aid according to the invention | Sipernat | Arbocel | Triameen YT | Sokalan PA 25 homopolymer (90% active) |
| --- | --- | --- | --- | --- | --- |
| 1 | 1 | 0 | 0 | 0 | 0 |
| 2 | 0 | 0 | 1 | 0 | 0 |
| 4 | 0 | 0 | 0 | 1 | 0 |
| 6 | 0 | 1 | 0 | 0 | 0 |
| Control | 0 | 0 | 0 | 0 | 1 |

Sipernat is a precipitated silica anticaking agent manufactured by Evonik Industries.

Arbocel is a low-friability powdered cellulose functional filler manufactured by Rettenmaier and Sohne.

Triameen YT is an alkyl triamine dispersing agent manufactured by Akzo Nobel Sokalan PA 25 homopolymer is an acrylic acid homopolymer dispersing agent manufactured by BASF.

Compacting Procedure

A closed-end cylindrical die under axial load from a vertical piston applied by an Instron universal testing machine (UTM) was used to compact the tablets. The ingredients were mixed according to each formulation described earlier and were compressed into 6 cm tablets with a mass of 53.2±0.8 g at 4500 N and 75° C. and held for 4 min. After forming, the tablets are cooled to room temperature and analyzed after 24 hours.

Test Procedures

Hardness:

Hardness was measured as the force required to break the dishwasher tablets (in kgf). The tablet is exposed to a gradually increasing force exercised by a metal bar of defined width (11 cm), over its entire diameter (6 cm) in an INSTRON force/displacement apparatus. The measurement is stopped automatically when the tablet breaks. The force applied at the breaking point is reported for the different tablets in kgf (force exerted by one kilogram of mass in standard gravity).

Friability:

The tablets are introduced into a sieve and shaken for a pre-set time of 15 min. The fines generated from the tablets by abrasion and impact pass through the sieve and are discarded. The tablets were weighed before shaking (initial weight) and after shaking (final weight) and the friability (%) calculated as shown below. The measurement was performed in duplicate.

$$\text{friability}(\%) = \frac{\text{Initial weight} - \text{final weight}}{\text{initial weight}} * 100$$

Disintegration:

The tablets are placed in a basket which is submerged in water-bath in circulating water at 60° C. (to simulate the dishwashing temperature) and attached to a scale. The decrease of weight over time is measured.

Results

Figure 1:
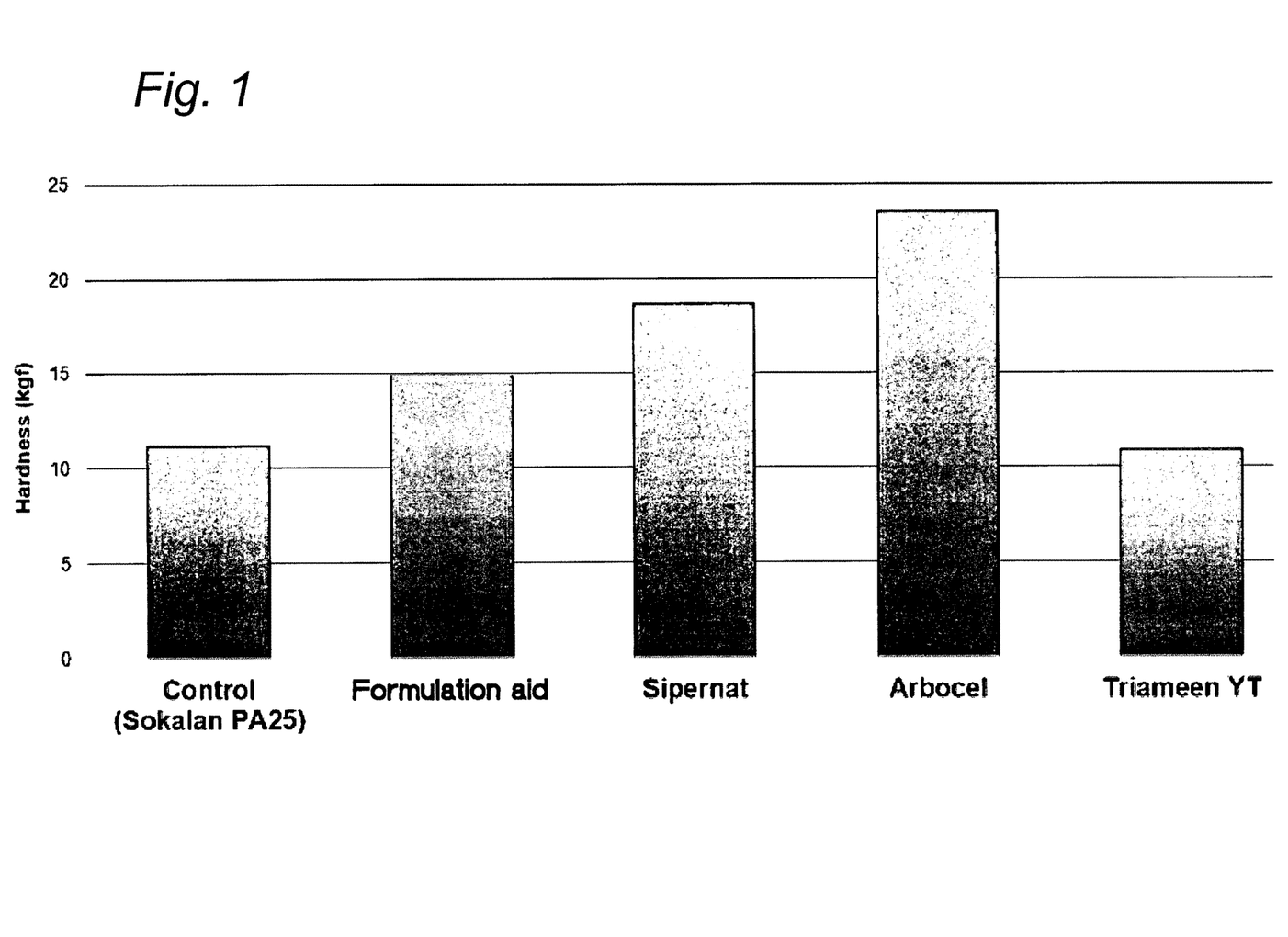
FIG. 1 shows the hardness measured for the tablets of example 2.

As shown in FIG. 1, the tablets containing formulation aid according to the invention provide sufficient hardness.

Figure 2:
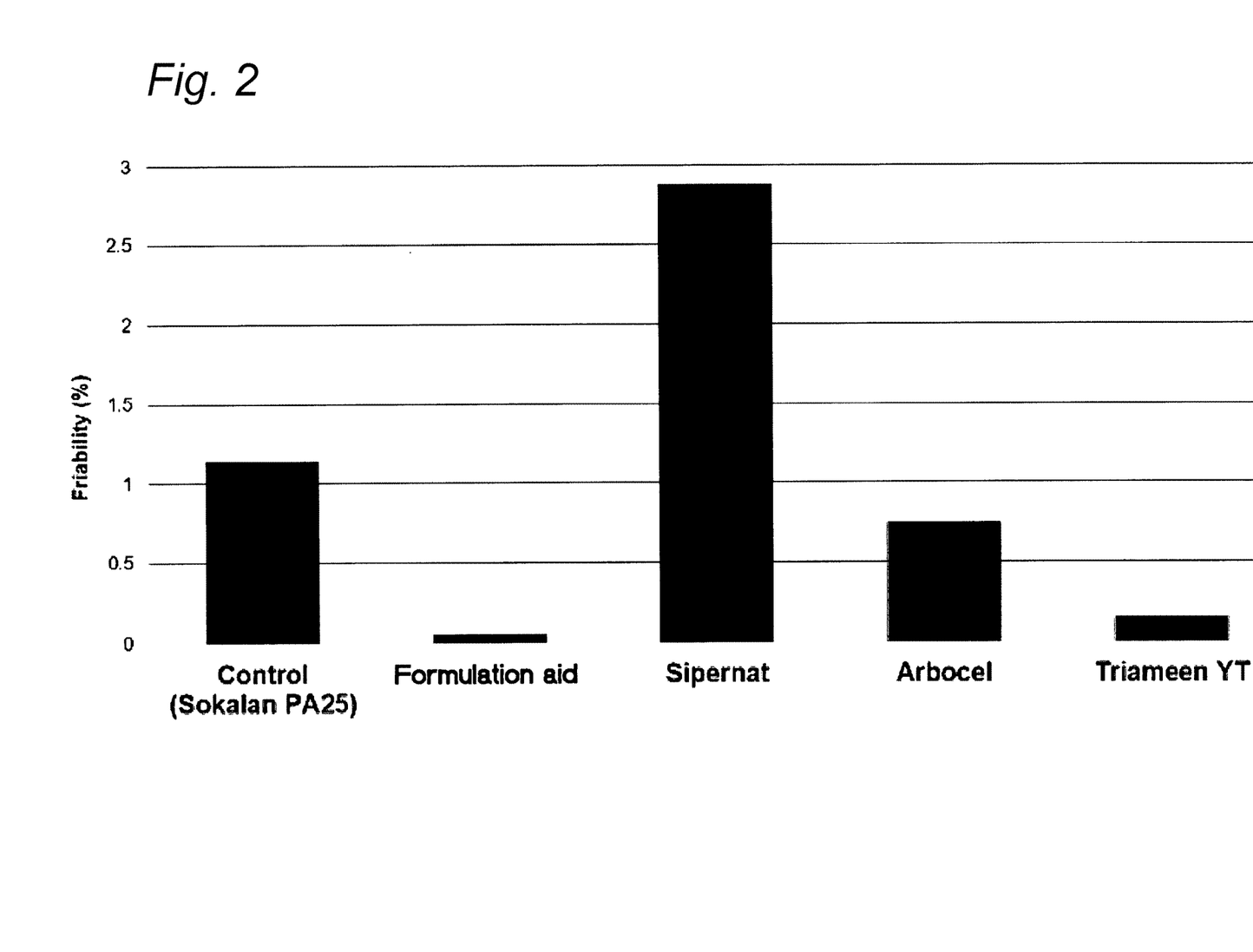
FIG. 2 shows the friability measured for the tablets of example 2.

As shown in FIG. 2, the tablets containing formulation aid according to the invention significantly outperformed alternative materials in relation to friability.

The results are indicative of the tablet's desirable ability to withstand breaking and abrasion in handling, packaging and shipment.

Figure 3:
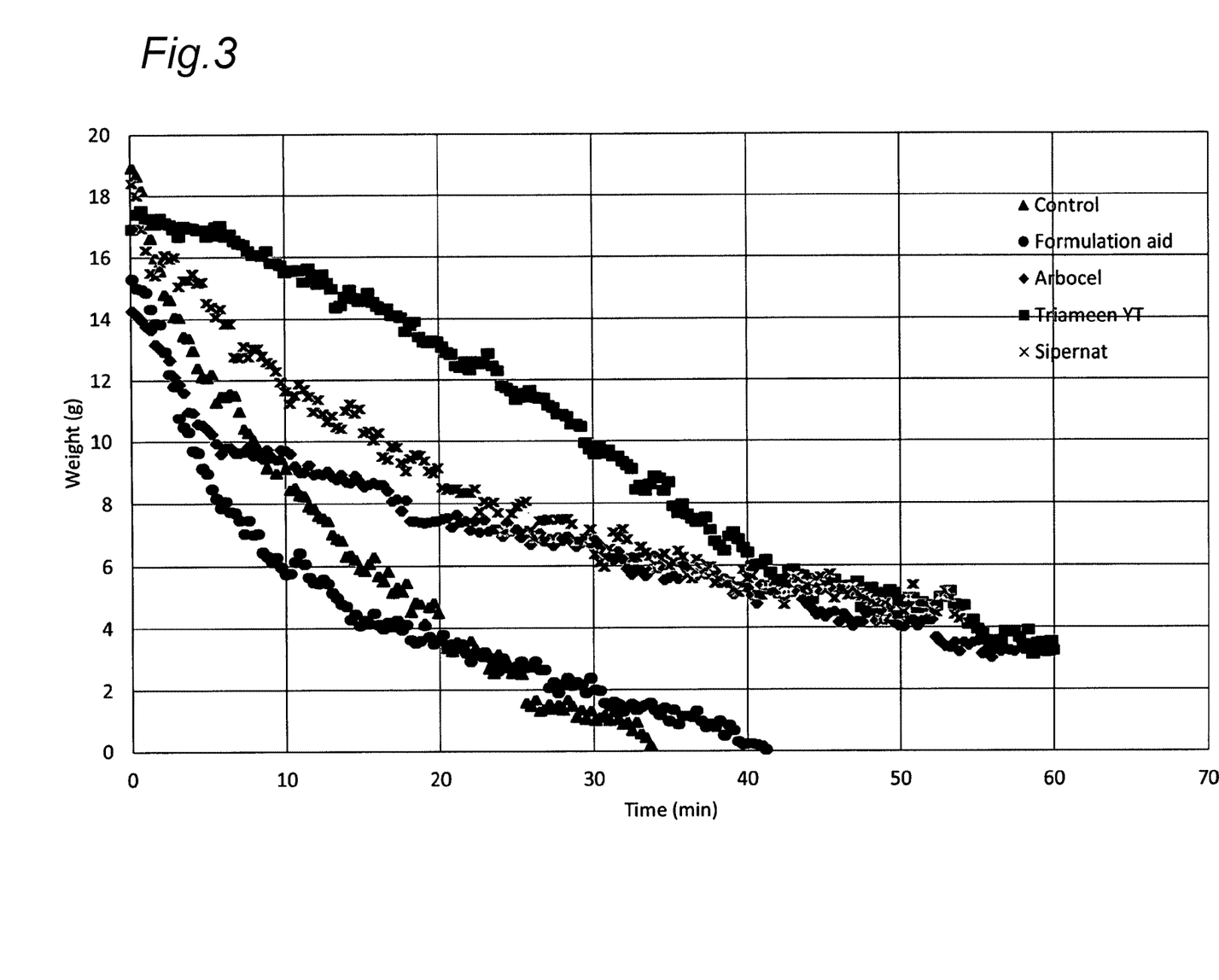
FIG. 3 shows the evolution of weight over time measured during the disintegration test of example 2.
Figure 4:
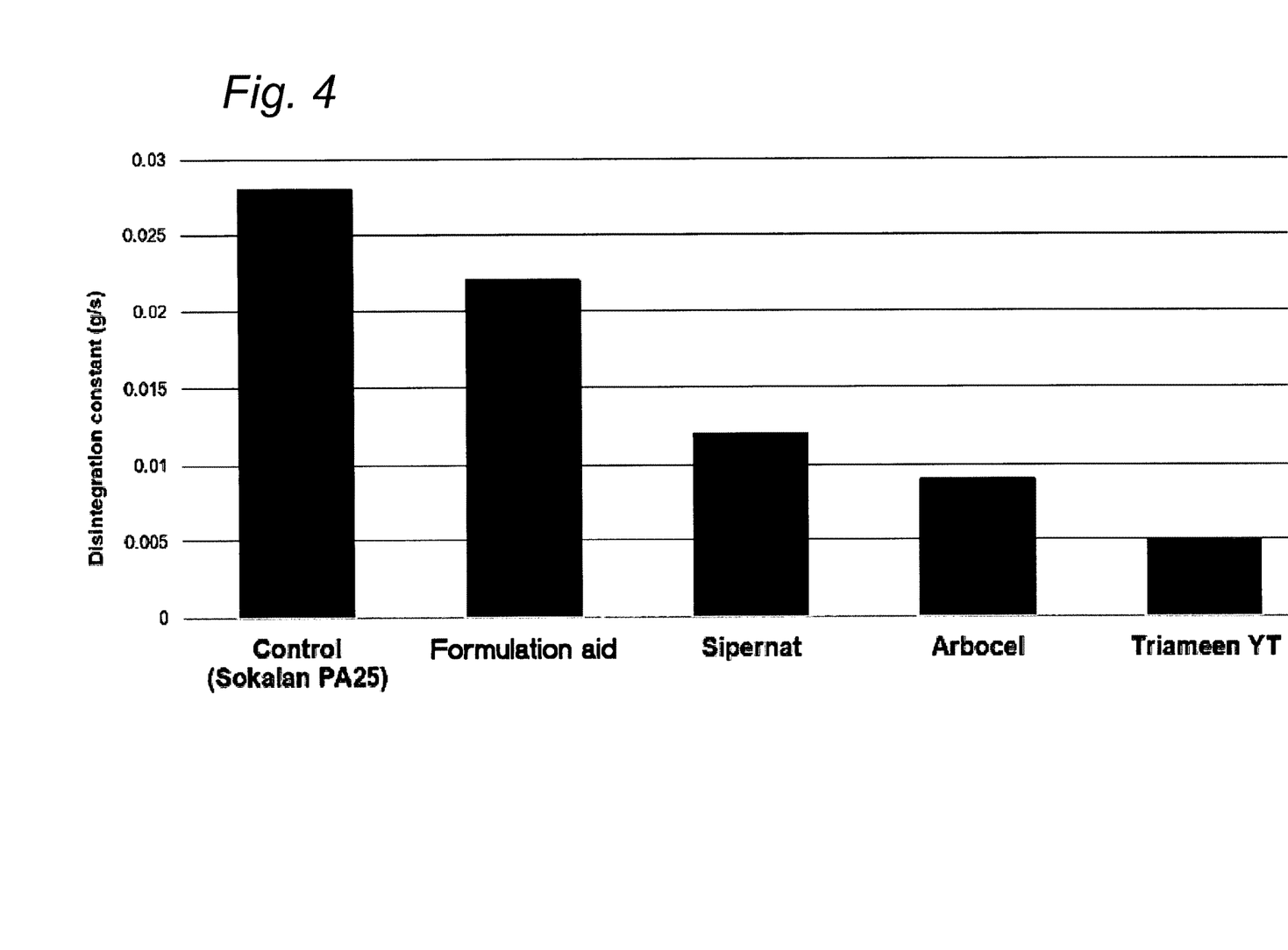
FIG. 4 shows the disintegration constant calculated for the tablets of example 3.

The disintegration constant represents the fraction of mass that disintegrates in 1 second and is calculated by transforming the weight data of FIG. 3 into $\text{Log}_{10}$ and then applying a linear model. As shown in FIG. 4, the monodisintegrant tablets containing formulation aid according to the invention possess a high disintegration constant, indicative of the ability to rapidly disintegrate in aqueous environments. This may be highly desirable in products such as dishwasher tablets in order to rapidly release active ingredients such as detergents into the environment.

Example 3—Anti-Caking Properties

Different formulations containing NaCl and the formulation aid (FA) of the present invention were prepared and stored in a controlled environment. The tendency of the different formulations to form agglomerates or cake was determined by visual inspection. The powder formulations shown in the table below were stored for 3 weeks at 20° C. and 60% relative humidity and inspected after 1 day, 1 week and 3 weeks.

|         | NaCl                  | NaCl + 0.1 wt % FA      | NaCl + 0.5 wt % FA    | NaCl + 1 wt % FA      |
|---------|-----------------------|-------------------------|-----------------------|-----------------------|
| 1 day   | moderate agglomerates | no agglomerates         | no agglomerates       | no agglomerates       |
| 1 week  | moderate agglomerates | moderate agglomerates   | no agglomerates       | no agglomerates       |
| 3 weeks | large agglomerates    | moderate agglomerates   | small agglomerates*   | small agglomerates*   |

*agglomerates fall apart easily

The invention claimed is:

1. A dishwashing tablet, comprising a formulation aid in the form of a powder from a parenchymal cell wall containing plant material in conjunction with one or more ingredients selected from the group consisting of phosphates, bleaching agents, ionic surfactants, non-ionic surfactants, enzymes, alkaline salts, anti-foaming agents, complexing agents, perfumes, anti-caking agents, starches, gelling agents, emulsifiers, dispersing agents and sand, wherein the formulation aid is obtainable by the method comprising:
    (a) obtaining a quantity of hydrated pulp composition derived from a parenchymal cell wall containing plant material;
    (b) drying the hydrated pulp, during which the temperature of the composition does not exceed 95° C.; and
    (c) subjecting the pulp to a milling or comminuting process to produce a powder, wherein said milling or comminuting process does not affect the primary, secondary and/or tertiary structures characteristic of parenchymal cell wall containing plant material in the pulp, to obtain a formulation aid in which the cell walls of the parenchymal cell wall containing plant material are intact at the primary, secondary and/or tertiary level.

2. The tablet according to claim 1, wherein the parenchymal cell wall containing plant material is sugar beet or chicory.

3. The tablet according to claim 1, wherein the formulation aid is obtainable by the method comprising:
    (a) obtaining a quantity of hydrated pulp composition derived from a parenchymal cell wall containing plant material;
    (b) thermal drying the hydrated pulp, wherein the composition is heated to a temperature within the range of 30-95° C. for a period of time sufficient to reach a dry matter content of greater than 90% by weight, based on the total weight of the pulp; and
    (c) subjecting the pulp to a milling or comminuting process to produce a powder, wherein said milling or comminuting process does not affect the primary, secondary and/or tertiary structures characteristic of parenchymal cell wall containing plant material in the pulp.

4. The tablet according to claim 1, wherein the formulation aid has a water holding capacity (WHC), as measured by AACCI 56-30, of greater than 7 ml/g.

5. The tablet according to claim 1, wherein the formulation aid has a bulk density of at least 400 g/l and a particle size distribution characterized by a D10 value within the range of 10-100 μm and/or a D90 value within the range of 400-600 μm, as measured by laser light diffractometry.

6. A laundry tablet, comprising a formulation aid in the form of a powder from a parenchymal cell wall containing plant material in conjunction with one or more ingredients selected from the group consisting of phosphates, bleaching agents, optical brighteners, ionic surfactants, non-ionic surfactants, enzymes, alkaline salts, anti-foaming agents, complexing agents, perfumes, anti-caking agents, starches, gelling agents, emulsifiers, dispersing agents, dye transfer inhibitors, fabric softeners and colorants, wherein the formulation aid is obtainable by the method comprising:
    (a) obtaining a quantity of hydrated pulp composition derived from a parenchymal cell wall containing plant material;

(b) drying the hydrated pulp, during which the temperature of the composition does not exceed 95° C.; and (c) subjecting the pulp to a milling or comminuting process to produce a powder, wherein said milling or comminuting process does not affect the primary, secondary and/or tertiary structures characteristic of parenchymal cell wall containing plant material in the pulp, to obtain a formulation aid in which the cell walls of the parenchymal cell wall containing plant material are intact at the primary, secondary and/or tertiary level.

7. The tablet according to claim 6, wherein the parenchymal cell wall containing plant material is sugar beet or chicory.

8. The tablet according to claim 6, wherein the formulation aid is obtainable by the method comprising:

(a) obtaining a quantity of hydrated pulp composition derived from a parenchymal cell wall containing plant material;

(b) thermal drying the hydrated pulp, wherein the composition is heated to a temperature within the range of 30-95° C. for a period of time sufficient to reach a dry matter content of greater than 90% by weight, based on the total weight of the pulp; and (c) subjecting the pulp to a milling or comminuting process to produce a powder, wherein said milling or comminuting process does not affect the primary, secondary and/or tertiary structures characteristic of parenchymal cell wall containing plant material in the pulp.

9. The tablet according to claim 6, wherein the formulation aid has a water holding capacity (WHC), as measured by AACCI 56-30, of greater than 7 ml/g.

10. The tablet according to claim 6, wherein the formulation aid has a bulk density of at least 400 g/l and a particle size distribution characterized by a D10 value within the range of 10-100 μm and/or a D90 value within the range of 400-600 μm, as measured by laser light diffractometry.

11. A fertilizer tablet comprising a formulation aid in the form of a powder from a parenchymal cell wall containing plant material in conjunction with one or more ingredients selected from the group consisting of ammonium compounds, urea compounds, magnesium compounds, potassium compounds, copper compounds, and zinc compounds, wherein the formulation aid is obtainable by the method comprising:

(a) obtaining a quantity of hydrated pulp composition derived from a parenchymal cell wall containing plant material;

(b) drying the hydrated pulp, during which the temperature of the composition does not exceed 95° C.; and (c) subjecting the pulp to a milling or comminuting process to produce a powder, wherein said milling or comminuting process does not affect the primary, secondary and/or tertiary structures characteristic of parenchymal cell wall containing plant material in the pulp, to obtain a formulation aid in which the cell walls of the parenchymal cell wall containing plant material are intact at the primary, secondary and/or tertiary level.

12. The tablet according to claim 11, wherein the parenchymal cell wall containing plant material is sugar beet or chicory.

13. The tablet according to claim 11, wherein the formulation aid is obtainable by the method comprising:

(a) obtaining a quantity of hydrated pulp composition derived from a parenchymal cell wall containing plant material;

(b) thermal drying the hydrated pulp, wherein the composition is heated to a temperature within the range of 30-95° C. for a period of time sufficient to reach a dry matter content of greater than 90% by weight, based on the total weight of the pulp; and (c) subjecting the pulp to a milling or comminuting process to produce a powder, wherein said milling or comminuting process does not affect the primary, secondary and/or tertiary structures characteristic of parenchymal cell wall containing plant material in the pulp.

14. The tablet according to claim 11, wherein the formulation aid has a water holding capacity (WHC), as measured by AACCI 56-30, of greater than 7 ml/g.

15. The tablet according to claim 11, wherein the formulation aid has a bulk density of at least 400 g/l and a particle size distribution characterized by a D10 value within the range of 10-100 μm and/or a D90 value within the range of 400-600 μm, as measured by laser light diffractometry.

16. A descaling tablet comprising a formulation aid in the form of a powder from a parenchymal cell wall containing plant material in conjunction with one or more ingredients selected from the group consisting of descaling agents, complexing agents, chelating agents, binders, fillers, acidic compounds such as hydrochloric acid, acetic acid, citric acid, glycolic acid, formic acid, phosphoric acid and sulfamic acid, wherein the formulation aid is obtainable by the method comprising:

(a) obtaining a quantity of hydrated pulp composition derived from a parenchymal cell wall containing plant material;

(b) drying the hydrated pulp, during which the temperature of the composition does not exceed 95° C.; and (c) subjecting the pulp to a milling or comminuting process to produce a powder, wherein said milling or comminuting process does not affect the primary, secondary and/or tertiary structures characteristic of parenchymal cell wall containing plant material in the pulp, to obtain a formulation aid in which the cell walls of the parenchymal cell wall containing plant material are intact at the primary, secondary and/or tertiary level.

17. The tablet according to claim 16, wherein the parenchymal cell wall containing plant material is sugar beet or chicory.

18. The tablet according to claim 16, wherein the formulation aid is obtainable by the method comprising:

(a) obtaining a quantity of hydrated pulp composition derived from a parenchymal cell wall containing plant material;

(b) thermal drying the hydrated pulp, wherein the composition is heated to a temperature within the range of 30-95° C. for a period of time sufficient to reach a dry matter content of greater than 90% by weight, based on the total weight of the pulp; and (c) subjecting the pulp to a milling or comminuting process to produce a powder, wherein said milling or comminuting process does not affect the primary, secondary and/or tertiary structures characteristic of parenchymal cell wall containing plant material in the pulp.

19. The tablet according to claim 16, wherein the formulation aid has a water holding capacity (WHC), as measured by AACCI 56-30, of greater than 7 ml/g.

20. The tablet according to claim 16, wherein the formulation aid has a bulk density of at least 400 g/l and a particle size distribution characterized by a D10 value within the range of 10-100 μm and/or a D90 value within the range of 400-600 μm, as measured by laser light diffractometry.

* * * * *